United States Patent [19]

Shimada et al.

[11] 3,966,830

[45] June 29, 1976

[54] PROCESS FOR THE NITRATION OF HALOGENATED BENZENE DERIVATIVES

[75] Inventors: Keizo Shimada; Takeo Nishikawa, both of Hino; Toshiaki Harada, Hachioji; Shizuo Nagahama, Hino, all of Japan

[73] Assignee: Teijin Limited, Osaka, Japan

[22] Filed: Nov. 12, 1974

[21] Appl. No.: 523,049

[30] Foreign Application Priority Data

Mar. 8, 1974 Japan.............................. 49-26340
Mar. 23, 1974 Japan.............................. 49-32221
Mar. 23, 1974 Japan.............................. 49-32222

[52] U.S. Cl. .............................................. 260/646
[51] Int. Cl.² ......................................... C07C 79/12
[58] Field of Search .................................. 260/646

[56] References Cited
OTHER PUBLICATIONS

Urbanski, Chemistry and Technology of Explosives, vol. 1, The MacMillan Co., New York, 1964, pp. 105 and 135.

*Primary Examiner*—Leland A. Sebastian
*Attorney, Agent, or Firm*—Sherman & Shalloway

[57] ABSTRACT

A process for nitrating halogenated benzene derivatives which comprises reacting in the vapor phase a halogenated benzene derivative with at least one member selected from the group consisting of nitric acid, nitrogen dioxide and nitrogen pentoxide in the presence of at least one solid inorganic oxide selected from the group consisting of silica, alumina and silica-alumina.

7 Claims, No Drawings

PROCESS FOR THE NITRATION OF HALOGENATED BENZENE DERIVATIVES

This invention relates to a process for the nitration of halogenated benzene derivatives.

Nitrated halogenated benzene derivatives are suitably used as intermediates for preparing various compounds. Of the nitrated halogenated benzene derivatives, the para-isomer of a monohalogenated mononitrobenzene is useful as an intermediate for the preparation of p-nitroaniline or p-phenylene diamine, which are important as materials for producing dyes or synthetic fibers. Furthermore, 1,2-dichloro-4-nitrobenzene (a nitration product of o-dichlorobenzene) and 2,5-dimethyl-1-chloro-4-nitrobenzene (a nitration product of 2,5-dimethyl-1-chlorobenzene) are also equally useful compounds.

Additionally, the ortho-isomer of halogenated nitrobenzene is likewise a useful compound.

According to the conventional method of nitrating halogenated benzenes with mixed acids, the ratio of 1-chloro-4-nitrobenzene to 1-chloro-2-nitrobenzene in the nitration product of monochlorobenzene, for example, is about 1.5 to about 1.8, and the nitration product contains 1 to 2% of 1-chloro-3-nitrobenzene. Hence, as its formation of the para-isomer is small, the foregoing conventional nitration method using mixed acids is unsuitable when the principal intended product is the para-isomer Further, the amount of formation of the ortho-isomer is insufficient, and hence the method also is unsuitable when the principal intended product is the ortho-isomer. Also, the foregoing conventional method has the drawback that there is the formation of a large quantity of spent acid diluted with the water formed from the reaction.

A method has been previously proposed which comprises nitrating monochlorobenzene in the presence of sulfuric acid and a carboxylic acid such as acetic acid to produce a larger proportion of the para-isomer (U.S. Pat. No. 3,180,900). This patent discloses that the ratio of p-isomer to o-isomer can be raised to as high as 2.9.

This method, however, is not entirely satisfactory for commercial operation, because the recovery of the spent sulfuric acid and carboxylic acid after the reaction is complicated.

A method of nitrating halobenzenes in which the o-isomer is formed in larger quantities than the conventional method using mixed acids is not known.

It is therefore an object of the present invention to provide an improved process for nitrating halogenated benzene derivatives, especially a process by which a nitration product containing the desired p-isomer or o-isomer in a favorable proportion can be obtained at a high conversion rate.

Another object of this invention is to provide a process for nitrating halogenated benzene derivatives which does not require treatment of the spent acid.

A further object of the invention is to provide a vapor phase process for nitrating halogenated benzene derivatives.

The foregoing objects of the present invention are achieved by a process of nitrating halogenated benzene derivatives which comprises reacting in the vapor phase a halogenated benzene derivative with at least one member of the group consisting of nitric acid, nitrogen dioxide and nitrogen pentoxide, in the presence of at least one solid inorganic oxide selected from the group consisting of silica, alumina and silica-alumina.

In accordance with the above-decribed invention process, the ratio of p-isomer to o-isomer of the product can be raised to at least 2.0, and under favorable conditions to at least 2.5.

The silica, alumina and silica-alumina, or a mixture of two or more of these components used in the present invention can be utilized after depositing thereon an oxyacid of sulfur. In this case the ratio of p-isomer to o-isomer can be raised to at least 2.0, and under suitable conditions to at least 2.5.

Further, the silica, alumina and silica-alumina, or a mixture of two or more of these components can be used after depositing thereon an oxyacid of phosphorus. In this case the amount formed of the o-isomer can be made greater than in the case of the conventional method, it being possible to raise the ratio of o-isomer to p-isomer to at least 0.8, and under suitable conditions to at least 0.9.

There has hitherto been suggested a method of nitrating a nonhalogenated aromatic hydrocarbon such as benzene in the vapor phase using either nitric acid or nitrogen dioxide in the presence of a phosphoric acid-supported alumina catalyst (See British patent specification No. 586,732, Soviet Patent No. 380,639 and Chemical Abstracts 79 52984Z). However, the method of nitrating in the vapor phase benzene derivatives whose nucleus has been substituted by a halogen atom, the nitration reaction of which is difficult, has not been known at all up to this time.

Hence, it is indeed surprising that according to this invention it has been found that halogenated benzene derivatives could be nitrated in the vapor phase by the action of either nitric acid, nitrogen dioxide or nitrogen pentoxide.

In the present specification, the p-isomer and o-isomer are defined as shown below and, accordingly, the p/o ratio denotes the molar ratio of the p-isomer to the o-isomer.

1. Monohalogenated mononitrobenzene derivatives:

Those having a nitro group in a position para to the halogen atom are defined as p-isomers, and those having a nitro group in a position ortho to the halogen atom as o-isomers.

2. Dihalogenated mononitrobenzene derivatives:

In the case of 1,3-dihalogenated compounds, those having a nitro group at the 4- or 6-position are defined as p-isomers, and those having a nitro group at the 2-position, as o-isomers. In the case of 1,2-dihalogenated compounds, those having a nitro group at the 4-position or 5-position are defined as p-isomers, and those having a nitro group at the 3-position or 6-position, as o-isomers.

3. Trihalogenated mononitrobenzene derivatives:

In the case of 1,2,3-trihalogenated compounds, those having a nitro group at the 5-position are defined as p-isomers, and those having a nitro group at the 4- or 6-position, as o-isomers. In the case of 1,2,5-trihalogenated compounds, those having a nitro group at the 4-position are defined as p-isomers, and those having a nitro group at the 3- or 6-position, as o-isomers.

Thus, in the present invention the halogenated benzene derivatives of the following formula are conveniently used.

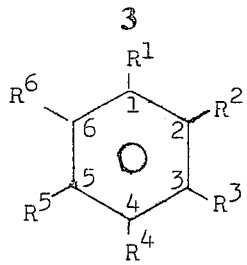

wherein R¹ is a halogen atom; R⁴ is a hydrogen atom; and R², R³, R⁵ and R⁶ are each a hydrogen atom, a halogen atom or an alkyl group, at least one of R², R³, R⁵ and R⁶ is a hydrogen atom, and the total number of halogen atoms including R¹ is not more than 3; with the provisos that when there is one halogen and both R³ and R⁶ are alkyl groups, R² is a hydrogen atom,; when there are two halogen atoms and R³ is a halogen atom, R² is a hydrogen atom; when there are two halogen atoms and R² is a halogen atom, at least one of R³ and R⁶ is a hydrogen atom; when there are three halogen atoms, R² is a halogen atom and R⁵ is a hydrogen or halogen atom; and when there are at least 2 halogen atoms including R¹, the substituent halogen atoms are substituted at positions such that the sum of the numbers 1 to 6 showing the substituting positions attached to the inside of the benzene ring in the above formula becomes a minimum.

Thus, the above formula does not include compounds which can produce only one kind of mononitro compound, such as a 1,4-dihalogenobenzene, a 1,3-dihalogen-2,5-dialkylbenzene, a 1,2,3-trihalogeno-5-alkylbenzene or a 1,3,5-trihalogenobenzene and compounds which cannot produce corresponding o-isomers, such as a 1-halogeno-2,3,6-trialkylbenzene, a 1,3-dihalogeno-2-alkylbenzene, a 1,3-dihalogeno-2,6-dialkylbenzene or a 1,2-dihalogeno-3,6-dialkylbenzene.

The catalyst used in this invention is a solid inorganic oxide chosen from silica, alumina, silica-alumina and a mixture of two or more of these components. The preferred forms of alumina are gamma-alumina or eta-alumina. Examples of silica-alumina inlude amorphous silica-alumina such as synthetic silica-alumina, acid clay and activated clay, and the crystalline synthetic and natural zeolites such as mordenite and Y-type zeolite.

The catalyst used in this invention includes those consisting of the foregoing solid inorganic oxides on which have been deposited oxyacids of sulfur and the salts thereof or the oxyacids of phosphorus.

As examples of the deposited oxyacids of sulfur and the salts thereof, mention can be made of sulfuric acid, pyrosulfuric acid, peroxysulfuric acid and the magnesium, aluminum, titanium, vanadium, chromium, manganese, iron, cobalt, nickel, copper, zinc, zirconium antimony and ammonium salts thereof. Examples of the deposited oxyacids of phosphorus include phosphoric acid, phosphoric acid anhydride, metaphosphoric acid, polyphosphoric acid, phosphorous acid and hypophosphoric acid. Of these acids and salts, especially preferred are sulfuric acid, phosphoric acid and the metal sulfates. Of the metal sulfates to be deposited, the sulfates having metallic ions of great electronegativity are especially to be preferred.

Electronegativity is a quality of an atom indicating the magnitude of its capacity to attract bond electrons, and it has been variously defined in the past by a number of persons. Herein will be used the electronegativity of metallic ions derived by K. Tanaka et al. [See *Shokubai* (Catalysis Society of Japan) 6, 262 (1964); *Shokubai Kogaku Koza* (Catalyst Engineering Course) 10; *Shokubai Benran* (Catalyst Handbook) Chijinshokan, p. 752] on the basis of the definition of Iczkowshi & Margrawe (See *J. Am. Chem. Soc.*, 83, 3547 (1961)). The electronegativities Xi of typical ions shown by K. Tanaka et al. are as follows:

Electronegativity of Metallic Ions (Xi)

|  | Xi |  | Xi |  | Xi |  | Xi |
|---|---|---|---|---|---|---|---|
| Li⁺ | 3.0 | Ni²⁺ | 9.0 | Rh³⁺ | 15.4 | Sn⁴⁺ | 12.6 |
| Na⁺ | 2.7 | Co²⁺ | 9.0 | Al³⁺ | 10.5 | U⁴⁺ | 15.3 |
| K⁺ | 2.4 | Fe²⁺ | 9.0 | Cr³⁺ | 11.2 | Ce⁴⁺ | 9.9 |
| Cu⁺ | 5.7 | Ca²⁺ | 5.0 | Co³⁺ | 12.6 | Ir⁴⁺ | 19.8 |
|  |  | Mg²⁺ | 6.0 | Fe³⁺ | 12.6 |  |  |
|  |  | Zn²⁺ | 8.0 | V³⁺ | 11.2 |  |  |
|  |  | Cu²⁺ | 9.5 |  |  |  |  |

In consequence of our detailed research into the nitration activity of metal sulfate catalysts, we found that there existed a strong correlation between the activity and the aforesaid electronegativity of metallic ions. That is to say, it was found that there was a tendency that as the electronegativity of the metallic ions forming the metal sulfates become higher, the catalytic activity became better. And we found that of the metal sufates usable as catalyst in the present invention the sulfates having metallic ions of electronegativity of above that of the magnesium ions (electronegativity 6.0) were especially superior in their catalytic activity. Further, when the aspect of cost was also considered, it became clear that sulfates such as of $Fe^{3+}$, $Cr^{3+}$, $Ni^{2+}$ and $Zn^{2+}$ were preferred.

It is recommended that the catalyst be used in the form of a powder, but it can also be in the form of pellets each having a diameter of 0.1 to 5 mm and a length of about 1 to 10 mm, or in the form of tablets each with a size of 1 to 10 mm.

The catalyst so prepared can be used as such for carrying out the reaction, but it is preferred that prior to its use it be calcined at a temperature of at least 100°C. A more preferred catalyst is prepared by impregnating the carrier with sulfuric acid or a salt thereof or phosphoric acid and then calcining it at a temperature of at least 100°C., preferably 100°C to 250°C., in the case of sulfuric acid or a salt thereof, and preferably 150° to 450°C. and more preferably 350° to 420°C., in the case of phosphoric acid.

The amount of the sulfuric acid or salts thereof or phosphoric acid to be deposited is about 2 to 0.1 times the weight of the silica, silica-alumina and/or alumina carrier, an especially preferred amount being about 1 to 0.2 times the weight of the carrier.

The sulfuric acid or salts thereof or phosphoric acid can be deposited on the carrier by any method, such as that of mixing the oxyacid or the salt with the carrier either as such or after dissolving or diluting it in or with water, or that of immersing the carrier in a solution of the oxyacid or the salt containing the acid or salt in excess, withdrawing the carrier from the solution and then drying it.

As nitration agents, nitric acid, nitrogen dioxide and nitrogen pentoxide are used in this invention. Again, mixtures of two or more of these compounds may also be used. Nitric acid used as nitrating agent in the process of this invention can be of any desired grade. It is however advantageous to use commercial grade concentrated nitric acid, and nitric acid having a specific gravity of about 1.3 to about 1.5 is a especially preferred.

Nitrogen pentoxide used in the invention process as nitrating agent is otherwise called nitric anhydride and can be obtained, for example, by adding fuming nitric acid to phosphorus pentoxide as shown by the following equation.

$$2 HNO_3 + P_2O_5 \rightarrow 2 HPO_3 + N_2O_5$$

It can also be obtained by the oxidation of liquid nitrogen tetroxide with ozone.

Nitrogen dioxide used in the invention process as a nitrating agent can be obtained by oxidizing NO or by thermally decomposing nitrogen pentoxide at above 260°C. as shown by the following reaction equation.

$$N_2O_5 \rightarrow 2 NO_2 + \tfrac{1}{2} O_2$$

While about 80% of the nitrogen dioxide is transformed into a dimer at about room temperature by the equilibrium reaction of the following equation, it is also known that almost all of it dissociates at above 150°C.

$$2 NO_2 \rightleftarrows N_2O_4$$

Nitrogen trioxide also dissociates as shown by the following equation and forms nitrogen dioxide and NO. Hence, it can be used as a nitrating agent in this invention, but since NO cannot be used as a nitrating agent, the yield per nitrogen atom declines.

$$N_2O_3 \rightleftarrows NO + NO_2$$

The halogenated benzene derivatives to be nitrated in accordance with the process of this invention include, for example, chlorobenzenes such as monochlorobenzene, o-chlorotoluene, m-chlorotoluene, o-chloroethylbenzene, o-chloropropylbenzene, monochloro-p-xylene, 1-chloro-2,3-dimethylbenzene, 1-chloro-3,5-dimethylenzene, 1-chloro-2,3,5-trimethylbenzene, o-dichlorobenzene, p-dichlorobenzene, 1,2-dichloro-3-methylbenzene, 1,2-dichloro-5-methylbezene, 1,2-dichloro-3,5-dimethylbenzene, 1,2-dichloro-5,6-dimethylbenzene, m-dichlorobenzene, 1,3-dichloro-5-methylbenzene, 1,3-dichloro-5-ethylbenzene, 1,3-dichloro-5,6-dimethylbenzene, 1,2,3-trichlorobenzene, 1,2,3-trichloro-6-methylbenzene, 1,2,5-trichlorobenzene, 1,2,5-trichloro-6-methylbenzene and 1,2,5-trichloro-3-methylbenzene; and the corresponding bromobenzenes. Of these compounds, those in which the total number of the halogen atoms and the alkyl groups is not more than 3 are preferred, especially preferred being the monohalogenated benzenes.

The vapor phase nitration of halogenated benzenes by the invention process is carried out by heating a reactor packed with the aforementioned catalyst to reaction temperature and then introducing therein a vaporized nitrating agent and the halogenated benzene. The reactor may be of either the fixed bed or fluidized bed type.

While the reaction is carried out in the vapor phase at a temperature above the boiling point of nitric acid, usually preferred is a temperature not exceeding 300°C. At higher temperature the decomposition of nitric acid becomes marked, and the yield of the nitration product is reduced.

The nitrating agent may be used in any proportion relative to the halogenated benzene, but it is usually used preferably in a range of 0.1 to 0.7 mol per mol of the halogenated benzene.

A carrier gas may be used in carrying out the reaction. Preferred as the carrier gas is nitrogen gas. The reaction mixture that has passed through the catalyst layer separates into a vapor phase and a liquid phase on cooling. The liquid phase is further separated into an organic phase consisting of the halogenated benzene and the nitration product thereof and a water phase containing unreacted nitric acid. The unreacted halogenated benzene and the product are obtained by isolating them from the organic phase by distillation. The resulting p-isomers and o-isomers are separated by fractional crystallization in the customary manner. The lower oxides of nitrogen contained in the vapor phase can be oxidized to nitric acid with air, then absorbed into the water phase and reused after concentration.

Thus, it is possible in accordance with the process of this invention to prepare by an extremely simple operation, and at a high conversion rate, a nitration product containing in a favorable proportion either the p-isomer or o-isomer as desired and moreover without the necessity of treating the resulting spent acid. Hence, this is a superior process for the nitration of halogenated benzenes.

The following examples will more specifically illustrate the invention. The parts in the examples are by weight.

EXAMPLE 1

Ten grams of concentrated sulfuric acid were absorbed onto 30 grams of gamma-alumina, after which the acid-adsorbed alumina was calcined for 1 hour at 200°C. to obtain 39.1 grams of the catalyst. Twenty-nine grams of this catalyst were packed in a quartz reaction tube and heated at 185°C. The reaction was then carried out for 5 hours by introducing into the top of this reaction tube 72% nitric acid (sp. gr. 1.42) and chlorobenzene at the rates of 5.5 grams per hour and 27.8 grams per hour, respectively. Mononitromonochlorobenzene was obtained at a per-pass yield of 56.5% relative to the nitric acid. The composition of the product was 77.5% p-isomers, 21.1% o-isomers and 1.4% m-isomers (p/o ratio = 3.6).

EXAMPLE 2

Ten grams of concentrated sulfuric acid were adsorbed onto 30 grams of a silica-alumina catalyst (alumina 13%, specific area 490 m²/g), followed by calcining for one hour at 200°C. to obtain 34 grams of the catalyst. 29 Grams of this catalyst were used, and the reaction was carried out for 7 hours at 215°C. by introducing 68% nitric acid (sp. gr. 1.40) and chlorobenzene at the rates of 6.4 grams per hour and 27.5 grams per hour, respectively. Nitrochlorobenzene was obtained at a per-pass yield of 57.3% relative to the nitric acid. The composition of the product was 68.8% p-isomers, 29.5% o-isomers and 1.7% m-isomers (p/o ratio = 2.3).

EXAMPLE 3

Ten grams of concentrated sulfuric acid were diluted with 30 parts of water, after which 30 grams of H-type mordenite (ZEOLON 200H produced by Norton Company) were dipped therein. Water was then evaporated from the so treated mordenite in a drier at 140°C., following which the dried mordenite was calcined for 4 hours at 200°C. to obtain 37.5 grams of the catalyst. Using 29 grams of this catalyst, the reaction was carried out for 6 hours at 185°C. by introducing 72% nitric acid and chlorobenzene at the rates of 6.8 grams per hour and 25.9 grams per hour, respectively. Nitrochlorobenzene was obtained at a per-pass yield of 64% relative to the nitric acid. The composition of the product was 69.6% p-isomers, 29.1% o-isomers and 1.3% m-isomers (p/o ratio = 2.4).

EXAMPLE 4–8

Experiments were carried out under the conditions indicated in Table 1, using as a catalyst sulfuric acid deposited upon solid inorganic oxides prepared as in Example 1. The results obtained are also shown in Table 1.

In the table, conversion is this mol% of the nitro chlorobenzene formed relative to the chlorobenzene fed, and yield is the mol% of nitrochlorobenzene formed relative to the nitric acid fed. These definitions apply equally when these terms are used in the subsequent tables.

relative to the nitric acid. The composition of the product was 71.0% p-isomers, 27.3% o-isomers and 1.6% m-isomers (p/o ratio = 2.6).

EXAMPLE 11

Thirty grams of gamma-alumina were dipped in a solution of 12.5 grams of copper sulfate ($CuSO_4 \cdot 5H_2O$) in 30 grams of water, following which the water was evaporated from the treated alumina in a drier at 140°C. and the dried alumina was calcined for 2 hours at 400°C. to prepare the catalyst. Using 29 grams of this catalyst, the reaction was carried out for 5 hours at 185°C. by introducing 70% nitric acid and chlorobenzene at the rates of 8.5 grams per hour and 27.9 grams per hour, respectively. Nitrochlorobenzene was obtained at a per-pass yield of 30% relative to the nitric acid. The composition of the product was 72.0% p-isomers, 26.1% o-isomers and 1.9% m-isomers (p/o ratio = 2.76).

EXAMPLE 12

The catalyst was prepared as in Example 10 by dipping 30 grams of gamma-alumina in a solution of 6.9

Table 1

| Experiment | Catalyst Kind | Amt. (g) | Reaction temperature (°C) | Nitric acid Conc. (%) | Nitric acid Amount used (g/hr) | Amount used of Monochlorobenzene (g/hr) | Mol % Nitric acid/ Monochlorobenzene | Conversion (%) | Yield (%) | Product composition o-isomer | m-isomer | p-isomer | p/o |
|---|---|---|---|---|---|---|---|---|---|---|---|---|---|
| Ex. 4 | $H_2SO_4$-H type mordenite | 29 | 187 | 72 | 6.44 | 25.9 | 32.0 | 18.0 | 56.3 | 70.5 | 1.5 | 28.0 | 2.52 |
| 5 | $H_2SO_4$-$SiO_2 \cdot Al_2O_3$ | " | 214 | 68 | 6.46 | 27.5 | 28.6 | 16.5 | 57.7 | 67.8 | 1.7 | 30.5 | 2.22 |
| 6 | $H_2SO_4$-$Al_2O_3$ | " | 185 | 72 | 5.56 | 27.8 | 25.7 | 14.1 | 54.9 | 77.5 | 1.4 | 21.1 | 3.67 |
| 7 | $H_2SO_4$-$SiO_2$ | 30 | 232 | 62 | 7.28 | 26.6 | 30.3 | 7.9 | 25.9 | 71.1 | 2.8 | 26.1 | 2.72 |
| 8 | $H_2SO_4$-$SiO_2$ | " | 172 | 62 | 4.73 | 30.7 | 17.1 | 8.3 | 48.8 | 69.0 | 1.6 | 29.4 | 2.35 |

EXAMPLE 9

Gamma-alumina powder and nickel sulfate ($NiSO_4 \cdot 6H_2O$) powder were mixed in equal amounts and then molded into tablets of 5-mm diameter, after which the tablets were calcined for 4 hours at 400°C. to prepare the catalyst. Twenty-nine grams of this catalyst were used, and the reaction was carried out for 3 hours at 200°C. by introducing 72% nitric acid and chlorobenzene at the rates of 4.9 grams per hour and 26.4 grams per hour, respectively. Nitrochlorobenzene was obtained at a per-pass yield of 27% relative to the nitric acid. The composition of the product was 74.9% p-isomers, 23.5% o-isomers and 1.6% m-isomers (p/o ratio = 3.2).

EXAMPLE 10

The catalyst was prepared in the following manner. Thirty grams of gamma-alumina were dipped in a solution of 14.38 grams of zinc sulfate ($ZnSO_4 \cdot 7H_2O$) in 30 grams of water, following which the water was evaporated from the treated alumina in a drier at 140°C. The dried alumina was then calcined for 2 hours at 400°C. The so obtained catalyst was used, and the reaction was carried out for 5 hours at 190°C. by introducing 70% nitric acid and chlorobenzene at the rates of 6.8 grams per hour and 27.9 grams per hour, respectively. Nitrochlorobenzene was obtained at a per-pass yield of 45% grams of sodium bi-sulfate in 30 grams of water. 29 grams of this catalyst were used, and the reaction was carried out for 5 hours at 280°C. by introducing 70% nitric acid and chlorobenzene at the rates of 5.8 grams per hour and 26.0 grams per hour, respectively. Nitrochlorobenzene was obtained at a per-pass yield of 35% relative to the nitric acid. The composition of the product was 72.5% p-isomers, 26.1% o-isomers and 1.4% m-isomers (p/o ratio = 2.8).

EXAMPLE 13

Thirty grams of a ferric sulfate ($Fe_2(SO_4)_3$-on-alumina catalyst prepared as in Example 12 were used, and the reaction was carried out for 5 hours at 176°C. by introducing 62% nitric acid and chlorobenzene at the rates of 5.28 grams per hour and 24.5 grams per hour, respectively. Nitrochlorobenzene was obtained at a per-pass yield of 42% relative to the nitric acid. The composition of the product was 72.3% p-isomers, 2.1% m-isomers and 25.6% o-isomers (p/o ratio = 2.82).

EXAMPLES 14–22

Thirty grams of a sodium sulfate ($Na_2SO_4$)-on-silica catalyst prepared as in Example 12 were used, and the reaction was carried out for 5 hours at 168°C. by introducing 62% nitric acid and chlorobenzene at the rates of 4.90 grams per hour and 29.8 grams per hour, respectively. Nitrochlorobenzene was obtained at a per-pass yield of 6.5% relative to the nitric acid. The composition of the product was 66.0% p-isomers, 2.9% m-isomers and 31.1% o-isomers (p/o ratio = 2.12).

In a similar manner, experiments (Examples 15–22) were carried out with catalysts consisting of silica deposited with various sulfates. The conditions of the reactions and the results obtained are shown in Table 2.

per-pass yield of 51% relative to the nitric acid. The composition of the product was 67.3% p-isomers, 31.1% o-isomers and 1.6% m-isomers (p/o ratio = 2.16).

Similarly, experiments (Examples 25–27) were carried out using catalysts consisting of silica-alumina deposited with various sulfates. The conditions of the reaction and the results obtained are shown in Table 3.

Table 2

| Experiment No. | Catalyst Kind | Amt. (g) | Reaction temperature (°C) | Nitric acid Conc. (%) | Nitric acid Amount used (g/hr) | Amount used of Monochlorobenzene (g/hr) | Mol % Nitric acid/ Monochlorobenzene | Conversion (%) | Yield (%) | o-isomer | m-isomer | p-isomer | p/o |
|---|---|---|---|---|---|---|---|---|---|---|---|---|---|
| Ex. 15 | MgSO$_4$-SiO$_2$ | 30 | 162 | 62 | 5.13 | 29.7 | 19.2 | 4.1 | 21.4 | 31.7 | 1.7 | 66.6 | 2.10 |
| 16 | NiSO$_4$-SiO$_2$ | " | 165 | " | 4.62 | 30.2 | 66.9 | 6.6 | 39.3 | 29.1 | 1.2 | 69.7 | 2.40 |
| 17 | Al$_2$(SO$_4$)$_3$-SiO$_2$ | " | 167 | " | 4.35 | 30.0 | 16.1 | 6.4 | 39.7 | 29.5 | 1.5 | 69.0 | 2.34 |
| 18 | Z$_n$SO$_4$-SiO$_2$ | " | 163 | " | 4.58 | 23.7 | 21.3 | 7.0 | 33.1 | 31.4 | 1.6 | 67.0 | 2.1 |
| 19 | Fe$_2$(SO$_4$)$_3$-SiO$_2$ | " | 167 | " | 4.15 | 29.4 | 15.5 | 8.1 | 53.4 | 24.8 | 1.7 | 73.4 | 2.96 |
| 20 | Cr$_2$(SO$_4$)$_3$-SiO$_2$ | 30 | 168 | 62 | 4.32 | 29.0 | 16.4 | 6.5 | 39.5 | 26.6 | 1.6 | 71.8 | 2.70 |
| 21 | Fe$_2$(SO$_4$)$_3$-SiO$_2$ | " | 170 | 98 | 5.64 | 26.4 | 37.4 | 17.3 | 46.3 | 30.5 | 1.3 | 68.2 | 2.24 |
| 22 | Fe$_2$(SO$_4$)$_3$-SiO$_2$ | " | 190 | 26 | 16.0 | 23.0 | 33.0 | 5.3 | 16.0 | 27.3 | 1.7 | 71.0 | 2.6 |

Table 3

| Experiment No. | Catalyst Kind | Amt. (g) | Reaction temperature (°C) | Nitric acid Conc. (%) | Nitric acid Amount used (g/hr) | Amount used of Monochlorobenzene (g/hr) | Mol % Nitric acid/ Monochlorobenzene | Conversion (%) | Yield (%) | o-isomer | m-isomer | p-isomer | p/o |
|---|---|---|---|---|---|---|---|---|---|---|---|---|---|
| Ex. 25 | CoSO$_4$-SiO$_2$.Al$_2$O$_3$ | 29 | 204 | 70 | 6.28 | 27.3 | 28.1 | 12.2 | 43.4 | 29.5 | 1.7 | 68.8 | 2.33 |
| 26 | MgSO$_4$-SiO$_2$.Al$_2$O$_3$ | " | 205 | " | 5.06 | 27.6 | 22.9 | 10.4 | 45.4 | 29.0 | 1.7 | 69.3 | 2.39 |
| 27 | VOSO$_4$-SiO$_2$.Al$_2$O$_3$ | " | 210 | " | 5.39 | 27.8 | 24.2 | 10.4 | 43.2 | 31.5 | 1.6 | 66.9 | 2.12 |

EXAMPLE 23

Thirty grams of synthetic silica-alumina (alumina 25%, specific area 400 m$^2$/g) were dipped in a solution of 6.6 grams of ammonium sulfate in 30 grams of water -dimethylbenzene, by drying at 140°C. and thereafter calcining for 3.5 hours at 400°C. to prepare the catalyst. Twenty-nine grams of this catalyst were used, and the reaction was carried out for 5 hours at 215°C. by introducing 70% nitric acid and chlorobenzene at the rates of 7.5 grams per hour and 28 grams per hour, respectively. Nitrochlorobenzene was obtained at a per-pass yield of 58% relative to the nitric acid. The composition of the product was 69.8% p-isomers, 28.5% o-isomers and 1.7% m-isomers (p/o ratio = 2.45).

EXAMPLES 24–27

Thirty grams of silica-alumina were immersed in a solution of 11.1 grams of aluminum sulfate in 30 grams of water followed by operating as in Example 23 to prepare the catalyst. Using 29 grams of this catalyst, the reaction was carried out for 5 hours at 190°C. by introducing 70% nitric acid and chlorobenzene at the rates of 6.0 grams per hour and 28 grams per hour, respectively. Nitrochlorobenzene was obtained at a

EXAMPLE 28

Twenty-nine grams of a solid phosphoric acid catalyst obtained by causing the adsorption of phosphoric acid onto diatomaceous earth followed by calcination were packed in a quartz reaction tube and heated at 265°C., after which the reaction was carried out for 10 hours by introducing into the top of the tube 72% nitric acid and chlorobenzene at the rates of 6.2 grams per hour and 27.9 grams per hour, respectively. Nitrochlorobenzene was obtained at a per-pass yield of 65% relative to the nitric acid. The composition of the product mononitromonochlorobenzene was 44.4% o-isomers, 2.2% m-isomers and 53.4% p-isomers.

EXAMPLE 29

Twenty-nine grams of the same solid phosphoric acid catalyst as that of Example 28 were used, and the reaction was carried out for 5 hours at 200°C. by introducing 68% nitric acid and chlorobenzene at the rates of 5.5 grams per hour and 29 grams per hour, respectively. Nitrochlorobenzene was obtained at a per-pass yield of 74% relative to the nitric acid. The composition of the product mononitromonochlorobenzene was 45.1% o-isomers, 1.6% m-isomers and 53.3% p-isomers.

EXAMPLE 30

13.5 grams of 85% phosphoric acid were adsorbed onto 30 grams of silica-alumina (alumina 13%, specific area 490 m²/g) followed by calcination of the silica-alumina for 1 hour at 300°C. to prepare the catalyst. Twenty-nine grams of this catalyst were used, and the reaction was carried out for 6 hours at 200°C. by introducing 70% nitric acid and chlorobenzene at the rates of 5 grams per hour and 27.5 grams per hour, respectively. Nitrochlorobenzene was obtained at a per-pass yield of 35% relative to the nitric acid.

EXAMPLE 31

Thirty grams of gamma-alumina were immersed in a solution of 15 parts of phosphorous acid in 15 parts of water followed by evaporating the water therefrom in a drier at 120°C. and thereafter calcining the gamma-alumina for 3 hours at 400°C. to obtain 41.8 grams of the catalyst. The reaction was then carried out for 6 hours by using 29 grams of this catalyst and introducing at 180°C. 13.2 grams per hour of 70% nitric acid and 27.5 grams per hour of chlorobenzene. Nitrochlorobenzene was obtained at a per-pass yield of 16% relative to the nitric acid.

EXAMPLE 32

Thirty grams of a silica-alumina catalyst (alumina 13%) were dipped in 30 grams of a 30% aqueous solution of hypophosphorous acid followed by evaporating the water therefrom in a drier at 120°C. and thereafter calcining the silica-alumina for 3 hours at 400°C. to obtain 41.3 grams of the catalyst. The reaction was then carried out for 5 hours by using 29 grams of this catalyst and introducing at 200°C. 70% nitric acid and chlorobenzene at the rates of 5.3 grams per hour and 27.3 grams per hour, respectively. Nitrochlorobenzene was obtained at a per-pass yield of 27% relative to the nitric acid.

EXAMPLES 33–36

The reactions were carried out by operating as in Example 28 but using as catalysts various carriers deposited with phosphorus compounds. The results obtained along with the conditions of the reactions are shown in Table 4.

Table 4

| Experiment No. | Catalyst Kind | Amt. (g) | Reaction temperature (°C) | Nitric acid Conc. (%) | Nitric acid Amt. used (g/hr) | Amount used of Monochlorobenzene (g/hr) | Mol % Nitric acid/ Monochlorobenzene | Conversion (%) | Yield (%) | Product composition o-isomer | m-isomer | p-isomer | p/o |
|---|---|---|---|---|---|---|---|---|---|---|---|---|---|
| Ex. 33 | H₃PO₃-Al₂O₃ | 29 | 280 | 68 | 9.88 | 27.6 | 43.5 | 2.3 | 5.3 | 28.5 | 4.4 | 67.1 | 2.35 |
| 34 | H₃PO₄-Kieselguhr | " | 203 | 72 | 5.13 | 27.5 | 24.0 | 17.8 | 74.2 | 44.1 | 1.6 | 54.2 | 1.28 |
| 35 | H₃PO₄-H-mordenite | " | 180 | " | 8.36 | 27.4 | 39.1 | 14.2 | 36.2 | 37.2 | 1.4 | 61.4 | 1.65 |
| 36 | AlPO₄-Al₂O₃ | " | 194 | " | 5.02 | 27.5 | 23.5 | 2.4 | 10.2 | 29.1 | 3.3 | 67.6 | 2.32 |

EXAMPLE 37

A quartz reaction tube was packed with 29 grams of a silica-alumina catalyst (alumina 13 wt. %, specific area 490 m²/g), and the reaction was carried out for 5 hours by maintaining the packed reaction tube at 280°C. and introducing 2.9 grams per hour of 68% nitric acid (sp. gr. 1.40) and 26.8 grams per hour of monochlorobenzene. The per-pass yield of the resulting monochloromononitrobenzene was 50% relative to the nitric acid, and its composition was 68.2% o-isomers, 28.2% p-isomers and 3.6% m-isomers, the p/o ratio being 2.4.

EXAMPLE 38

Twenty-nine grams of N-type mordenite were used, and by operating as in Example 37 the reaction was carried out for 5 hours by introducing at 150°C. 68% nitric acid at the rate of 5.2 grams per hour and chlorobenzene at the rate of 27.7 grams per hour to obtain monochloromononitrobenzene at a per-pass yield of 48% relative to the nitric acid. The composition of the product was 72.0% p-isomers, 26.8% o-isomers and 1.2% m-isomers, while the p/o ratio was 2.7.

EXAMPLES 39–45

The reactions were operated as in Example 37 but using the catalysts shown in Table 5. The results obtained along with the conditions of the reactions are shown in Table 5.

Table 5

| Experiment No. | Catalyst Kind | Amt. (g) | Reaction temperature (°C) | Nitric acid Conc. (%) | Nitric acid Amt. used (g/hr) | Amount used of Monochlorobenzene (g/hr) | Mol % Nitric acid/ Monochlorobenzene | Conversion (%) | Yield (%) | Product composition o-isomer | m-isomer | p-isomer | p/o |
|---|---|---|---|---|---|---|---|---|---|---|---|---|---|
| Ex. 39 | SiO₂ Al₂O₃ | 29 | 220 | 68 | 2.90 | 26.8 | 13.1 | 6.6 | 50 | 29.5 | 2.0 | 68.5 | 2.32 |
| 40 | γ-Al₂O₃ | " | 206 | " | 5.22 | 27.8 | 22.8 | 3.3 | 14.5 | 26.9 | 3.6 | 69.5 | 2.58 |
| 41 | H-mordenite | " | 220 | " | 5.17 | 27.7 | 22.7 | 10.7 | 47.1 | 27.3 | 1.3 | 71.4 | 2.62 |
| 42 | H-mordenite SiO₂.Al₂O₃ | 5.8 23.2 | 230 | 72 | 5.53 | 27.7 | 25.7 | 8.3 | 32.4 | 27.3 | 2.2 | 70.5 | 2.58 |
| 43 | SiO₂ (silicagel) | 30 | 160 | 62 | 7.42 | 29.0 | 29.0 | 6.2 | 21.5 | 31.9 | 1.6 | 66.5 | 2.09 |

Table 5-continued

| Experiment No. | Catalyst Kind | Amt. (g) | Reaction temperature (°C) | Nitric acid Conc. (%) | Nitric acid Amt. used (g/hr) | Amount used of Monochlorobenzene (g/hr) | Mol % Nitric acid/Monochlorobenzene | Conversion (%) | Yield (%) | Product composition o-isomer | m-isomer | p-isomer | p/o |
|---|---|---|---|---|---|---|---|---|---|---|---|---|---|
| Ex. 44 | SiO₂ (silicagel) | 30 | 220 | 62 | 7.88 | 30.5 | 30.5 | 3.0 | 10.0 | 26.9 | 2.9 | 70.2 | 2.61 |
| 45 | " | " | 273 | " | 8.11 | 31.5 | 31.5 | 1.9 | 6.0 | 25.6 | 11.8 | 62.6 | 2.44 |

EXAMPLE 46

Thirty grams of a ferric sulfate Fe₂(SO₄)₃-on-silica catalyst were used, and the reaction was carried out for 6 hours at 185°C. by introducing NO₂ gas at the rate of 0.19 equivalent per hour, calculated as elemental nitrogen, and chlorobenzene at the rate of 23.1 grams per hour. The per-pass yield and conversion of chlorobenzene relative to NO₂ gas were 10.7% and 9.8%, respectively. The composition of the product was 68.6% p-isomers, 3.4% m-isomers and 28.0% o-isomers (p/o ratio = 2.45).

EXAMPLE 47

The reaction was carried out for 6 hours at 164°C. using the same catalyst as that used in Example 46 and by introducing N₂O₅ gas at the rate of 0.24 equivalent per hour, calculated as elemental nitrogen, and chlorobenzene at the rate of 28.2 grams per hour. The per-pass yield and conversion of chlorobenzene were respectively 9.8% and 9.5% relative to the N₂O₅ gas. The composition of the product was 71.4% p-isomers, 1.3% m-isomers and 27.3% o-isomers (p/o ratio = 2.61).

EXAMPLE 48

Thirty grams of the same solid phosphoric acid catalyst as that of Example 28 were packed in a quartz reaction tube, and the reaction was carried out for 6 hours at 200°C. by introducing m-chlorotoluene at the rate of 43.8 grams per hour and 70% nitric acid at the rate of 6.5–7.0 grams per hour. After washing the organic layer of the reaction product in water, it was analyzed by gas chromatography. The composition of the product was as follows:

| | |
|---|---|
| 3-chloro-2-nitrotoluene | 12% |
| 3-chloro-4-nitrotoluene | 34% |
| 3-chloro-5-nitrotoluene | 2% |
| 3-chloro-6-nitrotoluene | 52% |

EXAMPLE 49

Thirty grams of a catalyst obtained by impregnating 30 grams of H-type mordenite with 10 grams of concentrated sulfuric acid followed by calcination were packed in a quartz reaction tube. The reaction was then carried out for 6 hours at 180°C. by introducing o-dichlorobenzene and 70% nitric acid at the rates of 50.8 grams per hour and 6.5–7.0 grams per hour, respectively. After washing the organic layer of the product with water, it was analyzed by gas chromatography. The proportion of 1,2-dichloro-4-nitrobenzene in the product was 90.2%.

EXAMPLE 50

Thirty grams of a catalyst obtained by impregnating 30 grams of silica gel with 9 grams of ferric sulfate followed by drying were packed in a quartz reaction tube, and the reaction was carried out for 3 hours at 170°C. by introducing p-chloroxylene and 60% nitric acid at the rates of 28 grams per hour and 5.6 grams per hour, respectively. The proportion of 2-chloro-5-nitrotoluene in the nitro-p-chlorotoluene contained in the product was 88.9%.

EXAMPLE 51

Thirty grams of a silica-alumina (alumina 25%) catalyst were packed in a quartz reaction tube, and the reaction was carried out by introducing 1-chlorotoluene and 70% nitric acid at the rates of 43.8 grams per hour and 6.5–7.0 grams per hour, respectively. After washing the organic layer of the product with water, it was analyzed by gas chromatography. The per-pass yield of the resulting chloronitrotoluene was 28.1% relative to the nitric acid, while the yield relative to the reacted chlorotoluene was 85%.

The composition of the product was as follows:

| | |
|---|---|
| 2-chloro-3-nitrotoluene | 18.5% |
| 2-chloro-4-nitrotoluene | 14.0% |
| 2-chloro-5-nitrotoluene | 48.0% |
| 2-chloro-6-nitrotoluene | 19.5% |

We claim:
1. A process for nitrating halogenated benzene derivatives which comprises reacting in the vapor phase a halogenated benzene derivative represented by the formula:

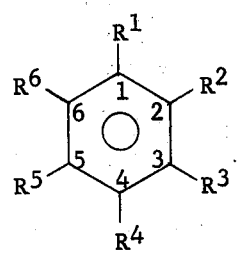

wherein $R^1$ is a halogen atom, $R^4$ is a hydrogen atom, and $R^2$, $R^3$, $R^5$, and $R^6$, independently represent a member selected from the class consisting of a hydrogen atom, a halogen atom and an alkyl group, at least one of $R^2$, $R^3$, $R^5$ and $R^6$ being a hydrogen atom, the total number of halogen atoms including $R^1$ being not more than 3; with the provisos that when there is one halogen atom and both $R^3$ and $R^6$ are alkyl groups, $R^2$ is a hydrogen atom; when there are two halogen atoms and $R^3$ is a halogen atom, $R^2$ is a hydrogen atom; when there are two halogen atoms and $R^2$ is a halogen atom, at least one of $R^3$ and $R^6$ is a hydrogen atom; when there are three halogen atoms, $R^2$ is a halogen atom and $R^5$ is a hydrogen or a halogen atom; and when there are at least two halogen atoms including $R^1$, the substituent halogen atoms are substituted at positions such that the sum of the numbers 1 to 6 showing the substituting positions attached to the inside of the benzene ring in the above formula becomes a minimum; with at least one member selected from the group consisting of nitric acid, nitrogen dioxide and nitrogen pentoxide in the presence of at least one solid inorganic oxide selected from the group consisting of silica, alumina and silica-alumina.

2. The process of claim 1 wherein said reaction is carried out in the presence of said solid inorganic oxide deposited with a compound selected from the group consisting of the oxyacids of sulfur, the salts thereof and the oxyacids of phosphorus.

3. The process of claim 1 wherein said reaction is carried out in the presence of a solid inorganic oxide obtained by impregnating said oxide with a compound selected from the group consisting of sulfuric acid, phosphoric acid and sulfates and thereafter calcining said impregnated oxide at a temperature of at least 100°C.

4. The process of claim 1 wherein said reaction is carried out in the presence of a solid inorganic oxide deposited with one or more sulfates having metallic ions of electronegativity equal to at least the magnesium ion.

5. The process of claim 1 wherein said halogenated benzene derivative is a chlorinated benzene derivative.

6. The process of claim 1 wherein at least two of $R^2$, $R^3$, $R^5$ and $R^6$ are hydrogen.

7. The process of claim 6 wherein $R^2$, $R^3$, $R^5$ and $R^6$ are each selected from the group consisting of hydrogen and alkyl.

* * * * *

UNITED STATES PATENT AND TRADEMARK OFFICE
CERTIFICATE OF CORRECTION

PATENT NO. : 3,966,830
DATED : June 29, 1976
INVENTOR(S) : SHIMADA, ET AL.

It is certified that error appears in the above-identified patent and that said Letters Patent are hereby corrected as shown below:

Claim 4, line 4, after "least" insert -- that of --

Signed and Sealed this

Second Day of November 1976

[SEAL]

Attest:

RUTH C. MASON
*Attesting Officer*

C. MARSHALL DANN
*Commissioner of Patents and Trademarks*